United States Patent
Hermansson et al.

(10) Patent No.: US 6,969,424 B2
(45) Date of Patent: *Nov. 29, 2005

(54) METHOD OF PRODUCING A CHEMICALLY BOUND CERAMIC PRODUCT, AND PRODUCT

(75) Inventors: Leif Hermansson, Uppsala (SE); Lars Kraft, Uppsala (SE); Bjarne Kjaerstad, Gjerdrum (NO); Daniel Hermansson, Gjerdrum (NO)

(73) Assignee: Doxa Aktiebolag, Uppsala (SE)

(*) Notice: Subject to any disclaimer, the term of this patent is extended or adjusted under 35 U.S.C. 154(b) by 108 days.

This patent is subject to a terminal disclaimer.

(21) Appl. No.: 10/240,502

(22) PCT Filed: Apr. 9, 2001

(86) PCT No.: PCT/SE01/00780

§ 371 (c)(1), (2), (4) Date: Oct. 3, 2002

(87) PCT Pub. No.: WO01/76534

PCT Pub. Date: Oct. 18, 2001

(65) Prior Publication Data

US 2003/0121454 A1 Jul. 3, 2003

(30) Foreign Application Priority Data

Apr. 11, 2000 (SE) .............................................. 0001321

(51) Int. Cl.⁷ ................................................. C04B 7/32
(52) U.S. Cl. ....................... 106/692; 106/695; 106/696; 106/35; 264/333
(58) Field of Search ................................ 106/692, 695, 106/696, 35; 264/333

(56) References Cited

U.S. PATENT DOCUMENTS

| 4,082,561 | A | * | 4/1978 | Nakagawa et al. | 106/695 |
| 4,647,600 | A | * | 3/1987 | Kawahara et al. | 523/116 |
| 4,652,593 | A | * | 3/1987 | Kawahara et al. | 523/116 |
| 4,689,080 | A | * | 8/1987 | Kawahara et al. | 106/35 |
| 5,234,497 | A | * | 8/1993 | Crocker | 106/695 |
| 5,269,845 | A | * | 12/1993 | Grunau et al. | 106/692 |
| 6,238,474 | B1 | * | 5/2001 | Unsin | 106/692 |
| 6,620,232 | B1 | * | 9/2003 | Kraft et al. | 106/404 |

FOREIGN PATENT DOCUMENTS

| EP | 0 559 627 A2 | 9/1993 |
| WO | WO 90/11066 | 10/1990 |

* cited by examiner

*Primary Examiner*—Paul Marcantoni
(74) *Attorney, Agent, or Firm*—Birch, Stewart, Kolasch & Birch, LLP

(57) ABSTRACT

Method for the production of a chemically bound ceramic material by means of reaction between a binding phase of one or more powdered binding agents and a liquid reacting with these binding agents, a quantity of powder containing said binding phase being suspended in said liquid so that all powder grains are brought into close contact with the liquid, whereupon the slurry thus obtained is drained so that the majority of surplus reacting liquid is removed, and is compacted during final draining, before the material is permitted to harden by reaction between said binding phase and the remaining liquid. One or more expansion-compensating additives, adapted to give the material dimensionally stable long-term properties, are mixed into said powder, prior to or in conjunction with its suspension in the liquid. The invention also relates to the product of the method.

54 Claims, 1 Drawing Sheet

METHOD OF PRODUCING A CHEMICALLY BOUND CERAMIC PRODUCT, AND PRODUCT

This application is the national phase under 35 U.S.C. §371 of PCT International Application No. PCT/SE01/00780, which has an International filing date of Apr. 9, 2001, and which designated the United States of America.

FIELD OF THE INVENTION

The present application relates to a method for producing a chemically bound ceramic material by means of reaction between a binding phase of one or more powdered binding agents and a liquid reacting with these binding agents, a quantity of powder comprising said binding phase being suspended in said liquid so that all powder grains are brought into close contact with the liquid, following which the suspension thus obtained is drained so that the majority of the surplus reacting liquid is removed and as a possible extra sub-step is finally drained, before the material is permitted to harden by reaction between said binding phase and the remaining liquid. The invention also relates to the chemically bound ceramic material which is obtained on execution of the method, and which is preferably used as dental filling material or as a carrier material (substrate) and casting material for producing replicas of electronic circuits, for example, and as a substrate material/casting material in the fields of micromechanics and biosensors and as a holder for optical fibres. In a special application, the material is used as inorganic putty.

BACKGROUND OF THE INVENTION

The present invention relates to binding agent systems of the cement system type, in particular the system $CaO$—$Al_2O_3$—$(SiO_2)$—$H_2O$. This system is used in the construction industry for exceptionally hard and tough environments, i.e. acid environments with high mechanical stress (R J Mangabhai, Calcium Aluminate Cements, Conference volume, E & F N Spon, London, 1990). By applying rupture mechanical attack methods and advanced powder technology to the system, the generally good profile of features of the base system can be improved considerably. Studies carried out according to the invention and previous works (SE 463 493 and 502 987) have produced a result that indicates great potential for the system for strong and acid-resistant materials such as dental filling materials and other applications. No dental filling material existing today meets all the requirements as regards biocompatibility, aesthetics and function that may be set by patients and dental service staff. The situation for various dental filling materials can be summarized as follows: Amalgam has generally good durability, but has shortcomings as far as biocompatibility and aesthetics are concerned. Plastic composites have good workability, but shortcomings with regard to erosion and corrosion and handling for staff (allergy problems have arisen). Plastic composites shrink on hardening, which gives rise to the risk of cracks forming and the onset of decay in the long run. Glass ionomers have a good bond with dentine and enamel, but shortcomings with regard to corrosion and strength. Silicate cement has good compressive strength and aesthetics, but suffers from corrosion and strength problems. Various types of inlay have good mechanical properties, but are labour-intensive and require gluing.

Below is a description of the requirements which should generally be set for a new, practical dental filling material; good handling ability with easy applicability in a cavity, moulding which permits good modellability, hardening/solidification which is sufficiently fast for filling work and serviceable directly following the visit to the dentist Furthermore, high strength and corrosion resistance exceeding that of existing filling materials are required, good biocompatibility, good aesthetics and safe handling for staff without allergy-inducing or toxic additives in the materials. In addition, good long-term characteristics with regard to dimensional stability are wanted. This is a problem in particular if the material expands over time, which can cause disastrous tooth breakages as a result.

DESCRIPTION OF THE BACKGROUND ART

In SE 463 493 it has been described how a chemically bound ceramic material, for e.g. dental purposes, can be caused to have enhanced strength characteristics in that a powder body consisting of one or more hydraulic binding agents and possible ballast material is compacted at such a high external pressure and so low a temperature that a closely connected raw compact is obtained without sintering reactions on compaction. In this raw compact, the filling density has increased to at least 1.3 times the initial filling density, which is defined as the filling density which is achieved by shaking, vibration and/or light packing of the loose powder in a container. The user of the material prepares the same by saturating the raw compact with a hydrating liquid prior to application of the material or in situ in a cavity, e.g. a tooth cavity.

The material produced according to SE 463 493 has indeed proved to satisfy most requirements that can be set according to the above for dental filling material. However, it has been found that problems can occur with dimensional changes, especially long-term expansion, which according to the above can have disastrous consequences in connection with dental fillings. There may also be a requirement for certain applications for a method of producing the ceramic material without raw compacts having to be used.

Following SE 463 493, it has been shown according to Swedish patent 502 987 that for cement systems complete hydration (which may possibly reduce the risk of dimensional changes) can take place if complete soaking and subsequent compacting of the cement system take place using a specially designed stopper. However, the method does not prevent dimensional changes which take place afterwards and which are related to phase transformations of hydrate or reactions with the surrounding atmosphere (for example, exhalation air with a higher carbon dioxide content), or other reactions. These reactions and related dimensional changes become more obvious in cases where a high degree of compactness is used in the production of the material. However, a higher degree of packing is normally sought, as this generally gives greater strength. A problem in this connection is to achieve a sufficient degree of compactness, for acceptable strength of the material produced, in spite of the fact that raw compacts are not used. At the same time, the degree of compactness may not be too high if the moist powder material is to be applied in the cavity, since this impairs mouldability. The method of manufacture can also be developed further, in particular made simpler and automated, and made more repeatable, which is desirable especially if the ceramic material is to be used for purposes other than dental ones.

In Yan et al, Characteristics of shrinkage compensation expansive cement containing prehydrated high alumina cement-based expansive additive, Cement and Concrete Research, Vol 24, p 267–276 (1990), the use of calcium aluminate's tendency to expand is described. This article and related works on expansive cements describe the possibilities of making standard cement expand or shrink less using calcium aluminates amongst other things, but do not touch on the problems of long-term expansion of highly compacted cement systems and control of the expansion of calcium aluminates at very low levels, which is a prerequisite for the use of these binding agent systems in applications according to the present invention.

Other immediate works and patents which do not however touch on the principle field of the present invention are for example SE-B-381 808, EP-A-0 024 056 and EP-A-0 115 058, DE 5 624 489 and U.S. Pat. No. 4,689,080.

DISCLOSURE OF THE INVENTION

One object of the present invention is to present a method for producing a chemically bound ceramic material of the type stated in the preamble, which method can be used to give a chemically bound ceramic material that has dimensionally stable long-term properties. The moist powder material must also satisfy the requirements set out above in respect of workability, and be easy to handle in connection with application in a cavity, e.g. a tooth cavity. The ceramic material formed should also, for dental or other applications, have high strength, and satisfy the demands that are made on such materials according to the above. Suitably, the method according to the invention should also be relatively easy to execute, as well as having good repeatability and being suitable for being automated to a high level for certain applications.

Advantages in the case of applications as a carrier material are generally the possibility of obtaining a simple, cost-effective production method, dimensional stability being achieved on hardening. The base materials for the products are also very favourable from the environmental and biological point of view. This means that this invention, which has been developed primarily for dental purposes, has major application areas as a substrate/casting material for electronics, micromechanics, optics and in biosensor technology. The environmental aspects in particular also give the material a large application range for a further application, to be precise as inorganic filler.

Composition of the Powder Mixture Including Additives

Apart from good mechanical properties, chemical attributes are important for dental applications. In a significant aspect of the invention, calcium aluminates, i.e. double oxides of CaO (calcium oxide) and $Al_2O_3$ (aluminium oxide)—here and below termed the CA system, which reacts with water, forming calcium aluminate hydrates—are used as the main binding phase. This hydration reaction constitutes the actual setting and hardening process. Conventionally, some type of aggregate (filler particle) is added to the calcium aluminate cement, principally for economic reasons. According to the invention, the choice of the CA cement system, combined with another cement system or phase which interacts with the aluminate cement, or combined with the addition of porous aggregates or soft materials, produces a dimensional change which is less than approx. 0.30% linearly, often less than 0.10%. In special cases, the dimensional change may be close to zero expansion.

According to a first embodiment of the invention, the CA system can be used as the only main binding phase or with the addition of another cement binding phase in amounts of less than 30 percent by volume. Admixtures of ordinary Portland cement (OPC cement) or fine-grained silicon dioxide are used advantageously. Since the calcium aluminate cement has a tendency to expand more strongly on harder packing, combinations of CA cement and another phase of said type, with a tendency to shrink, can produce reduced dimensional changes. The CA cement should be present in dental applications as the main phase in the binding phase, as the CA phase contributes to high strength and acid resistance.

It has proved to be the case that the theories regarding reasons for dimensional changes which were put forward in connection with Swedish patent 502 987, i.e. incomplete hydration, do not appear to give a full explanation of the reasons behind the problems with regard to dimensional stability. The background to the present invention is rather the idea that the dimensional changes are linked to phase transformations of hydrates. The statement, which is not to be seen as restrictive for the invention, means that calcium aluminate, when it begins to dissolve on the addition of water, forms a gel which then crystallizes and forms hydrate phases. Due to continued hydration reactions and hydrate transformations, various pure Ca aluminate hydrates such as 10-phase, 8-phase, other less defined hydrate phases or transition phases, and finally 6-phase (katoite) can be present, and in the case of additives containing silicon, Ca—Si aluminate hydrate. 10-phase, 8-phase and 6-phase refer to calcium aluminate phases with 10, 8 or 6 water of crystallization per unit of formula respectively. Phase transformation of the hydrates can lead to dimensional changes, especially expansion, which has been shown by long-term evaluation of cement materials. It has turned out surprisingly to be the case in connection with the present invention that with the addition of a secondary phase containing silicon, preferably ordinary so-called Portland cement (OPC cement with Ca-silicates as main phases) and/or fine crystalline silicon dioxide (which constitutes said first, preferred embodiment of the invention), undesirable phase transformations or changed phase transformation sequences can be avoided in the main, and as a direct consequence of this dimensional changes can be minimized, especially long-term expansion. How the complicated hydration reactions come about in detail is not entirely explained. With the addition of material containing Si, the hydration reactions are modified, leading to dimensionally stable materials.

Surprisingly, it has been found that the positive effects just mentioned on the addition of a secondary phase have an optimum with relatively low addition quantities. The minimum expansion has been attained in this connection when said secondary phase consists of OPC cement and/or fine crystalline silicon dioxide and/or another phase containing Si, preferably in a total content of 1–20 percent by volume and even more preferredly 1–10 percent by volume in the material. Most preferredly, said secondary phase consists of OPC cement in a quantity of 1–5 percent by volume and/or fine crystalline silicon dioxide in a quantity of 1–5 percent by volume. Reference is also made in this context to the examples in this specification.

It has also turned out surprisingly that conventional filler particles providing hardness, e.g. in the form of hard $Al_2O_3$ particles, can be avoided entirely in the material, or that their use can be minimized, since it is hydrate transformations which are the primary cause of dimensional changes over time, especially long-term changes. Furthermore, the hardness is primarily related to the binding phases and not to inert additives, even if these have a high hardness in themselves. The expansion-compensating additives according to the invention act here on the cement phase, without the influence of any hardness-providing filler particles which may be present. Being able to avoid or minimize the use of hardness-providing filler particles is also due to the fact that any unreacted cement remaining—which was previously considered serious from the expansion viewpoint—only has a slight effect on the expansion. It has been found in connection with the invention that unreacted cement can instead work positively, as an in-situ filler material, which contributes to the desired hardness of the material.

According to one embodiment of the invention, however, the powder mixture, and thus the finished ceramic material, can contain ballast material, which does not take part in the chemical reactions between the binding phase and the hydration liquid, but which is present as a solid phase in the finished ceramic product. According to one aspect of the invention, the powder mixture can therefore contain up to 50 percent by volume of ballast material. This ballast material can for example be of the type described in SE 463 493 and SE 502 987, i.e. fibres of metal, carbon, glass or organic material etc., or continuous crystals, so-called whiskers, of e.g. SiC, $Si_3N_4$ and/or $Al_2O_3$.

According to another embodiment of the invention, due to additions of aggregates (filler particles) of a given geometry/shape, porosity and/or softness, the dimensional stability of binding agent systems of interest can be monitored precisely and justified to desired levels, often to low levels or to no dimensional change at all. The situation for the cement system $CaO—Al_2O_3—(SiO_2)—H_2O$, which can be used to advantage as a base material for dental filling material, is described in greater detail below, but the invention relates generally to ceramic binding agent systems in which dimensional stability is critical.

By selecting aggregates (filler particles) in binding agent systems according to the present invention with a specific geometry and porosity, the binding conditions between the binding phase and aggregates can be influenced positively, like the dimensional stability. Porous aggregates and other expansion- or shrinkage-compensating additives thus contribute to the possibilities of being able to justify dimensional changes to a desired level by acting as "expansion vessels".

The function of porous aggregates according to the present invention is thus, with the retention of a high given content of filler particles, to increase the contact surface with the cement phase and distribute this on a smaller propagation area. The expansion which derives from the cement phase is taken up primarily by the porous filler particle in that the cement is given the opportunity to expand inside this. Porous aggregates can consist advantageously of inert ceramic materials such as aluminium oxide, zirconium oxide, titanium oxide or zinc oxide or another oxide or a combination of oxides. The porosity can be present as open or closed porosity or in a combination. In the normal case, the porous particle or aggregate has an open porosity of 20–60%, preferably 30–50%. An aggregate size is chosen which is optimally suited to the rupture strength of the materials, but often it has a diameter of less than 20 $\mu$m, preferably 5–15 $\mu$m. Small porous aggregates or particles contribute in materials of immediate interest to finer surfaces (lower $R_a$-values) than solid particles of a corresponding size. The pore openings in the aggregates are adapted to the penetration capacity of the binding agents. The pore openings are advantageously less than 5 $\mu$m, preferably 0.1–5 $\mu$m and even more preferredly 1–3 $\mu$m.

Porous aggregates or particles of the above named oxides are produced preferably by sintering fine-grained powder, but not at temperatures too high for the aggregates or particles to be kept porous. Aluminium oxide, for example, is suitably sintered at around 1500–1600° C. The sintering process is controlled to the desired diameter, porosity and size of pores. Alternatively, the porous aggregates or particles can be produced by mixing fine-grained oxide powder with an agent, e.g. starch, which is made to evaporate so that pores are formed. The material is freeze-granulated by being sprayed and frozen.

In a special case to be able to take up inner stresses caused by dimensional changes in the binding phase, aggregates with a very high closed porosity can be used, which breaks in the event of high internal stress and provides internal expansion space. The content of these highly porous particles is limited to a maximum of 5 percent by volume of the binding agent phases. Highly porous microspheres of glass can be used in this case. The highly porous materials are added to the cement mixture in the final step of the mixing operation to avoid being ground down. In another special case, a very soft particle is chosen as an extra additive, which particle can take up stresses by having an E-modulus lower than that of the binding phase. Various soft polymers, e.g. plastic balls, or hydrate can be used here. When using plastic balls, which are very small, these may also have holes in the middle for further deformability.

According to an aspect of the invention, it has also been found that the dimensional stability of the material can be increased by causing the constituent components to have a highly fine granularity. This also applies to strength aspects. The theory in that case is that particles that are too large have a tendency to lie constricted in the structure, with different accompanying attributes in different directions. According to this aspect of the invention, a fine-grained, finely divided mixture of binding agent raw materials is therefore used, which gives a fine homogeneous microstructure. Small propagation areas for the constituent phases reduce the inner mechanical stress between the phases, and provide a better opportunity to compensate for the internal expansion which can take place in the event of changes of phases, such as continued reaction with the surroundings or phase transformations. The size which can be permitted depends on the level of strength desired, but the grain size should typically lie with a distribution over 0.5–10 $\mu$m. The calcium aluminate is caused by grinding to have a grain size in the main of around 2–8 $\mu$m, preferably 3–4 $\mu$m or around 3 $\mu$m, and OPC cement, if this is used, is caused by grinding to have a grain size in the main of around 4–8 $\mu$m, preferably 5–7 $\mu$m or around 6 $\mu$m. Fine-grained silicon dioxide, if such is used, would have an even smaller grain size, preferably in the order of magnitude of less than 100 nm, and even more preferredly around 10–50 nm, e.g. around 15 nm, which type of silicon dioxide can be purchased for example as a commercial product, separated in electrostatic filters in the production of silicon.

According to one aspect of the invention, the powder mixture can be made to contain an accelerator for an accelerated reaction between said binding agents and the liquid, preferably a salt of an alkali metal, preferably a salt of lithium, e.g. lithium chloride or lithium carbonate, or lithium hydroxide, in a quantity of 0.1–0.5 per mil by volume, preferably 0.2–0.3 per mil by volume calculated on the solid contents. The powder mixture can possibly also be made to contain a liquid-reducing agent, preferably a lignosulfonate and/or citrates, substances with hydroxycarboxyl groups. The advantage of using liquid-reducing agents is that a smaller quantity of hydration liquid is required, which means in this context that a smaller amount of liquid needs to be drained.

Suspension

The solid constituent parts according to the above are mixed well, suitably in the presence of a non-polar and/or hydrophobic liquid, e.g. petroleum ether, acetone or isopropanol, whereupon this non-polar liquid is evaporated from the mixture. A quantity of powder mixture adjusted to the purpose, containing additives, is then suspended in a quantity of hydration liquid, normally water, matched to the quantity of powder mixture. The liquid can contain an accelerator here for a higher hardening rate and increased final strength, and possibly a liquid-reducing agent. In particular, if the powder mixture does not contain additives of this kind, they can instead be used in the liquid. The accelerator consists preferably of a salt of an alkali metal, preferably a salt of lithium, e.g. lithium chloride or lithium carbonate, in a quantity of 0.2–2 g/l and the liquid-reducing agent consists preferably of a lignosulfonate and/or citrate, EDTA, hydroxycarboxyl-containing compounds in a quantity exceeding 0.1% calculated on the liquid. In the suspension, all powder grains are brought into close contact with the liquid. The liquid content can be reduced by up to around 50% while retaining the same low viscosity when using liquid-reducing agents (English: superplasticisers).

Preliminary Draining

When the powder mixture has been suspended in the liquid, the slurry is transferred to a porous, absorbent bed for preliminary draining. The slurry is suitably transferred in this connection to a limited area, as defined for example by a circular-cylindrical wall, without a bottom, placed on a hard, porous surface. This surface is formed preferably by one side of a plate of a porous ceramic material, a porous metal material, a porous polymer material or a porous wood material, most preferredly a porous ceramic material. To increase the effect of the initial predraining, the slurry can be pressed lightly against the porous surface as a second step in the predraining, so that a primary surplus of the liquid is sucked into the porous material. The initial predraining is thus executed preferably under pressure, suitably a pressure of less than 10 MPa. Another porous surface is used as a pressing surface on the side of the slurry opposite the porous plate, which porous surface is preferably formed by one side of a pressing device of a porous ceramic material, a porous metal material, a porous polymer material or a porous wood material, most preferredly a porous wood material, which preferably consists of beech wood or another hardwood material.

Following the initial predraining, the moist powder mixture normally has a degree of compactness of 35–50 percent by volume solid phase, depending on whether only step 1 or both step 1 and 2 have been used.

If the ceramic material produced is to be used as inorganic putty, e.g. in the car industry as a filling compound on resprays etc., only step 1 of the initial predraining step just mentioned is advantageously used, the slurry thus being drained on a porous plate, preferably without pressure applied. This is particularly favourable in the event that liquid-reducing agents are used, a higher degree of compactness being obtained due to the reduced quantity of water.

If the ceramic material produced is to be used for other purposes, without being packed together in a cavity, it is also preferred to use only step 1 of the initial draining or to let the initial draining be executed in the same step as the subsequent compaction. The whole manufacturing process is suitably automated in this connection, including suspension, draining and compaction.

Compaction

When the slurry is subjected to any initial draining according to the above, it is compacted to a final degree of compactness of 47–60 percent by volume solid phase, preferably >51 percent by volume solid phase, and even more preferredly >55 percent by volume solid phase. It is to be noted that these degrees of compactness in certain cases can refer to weighted average values for constituent phases. Compaction can take place in one, two or more steps. Compaction can be executed in a manual press or an automated press.

The area for the slurry, i.e. the circular cylindrical wall containing the slurry, is placed in a mechanical pressing tool comprising at least one, preferably at least two, surfaces acting against the moist powder mixture. This or these surfaces are formed by a hard porous material, into which a surplus of the liquid is sucked, said hard, porous material preferably consisting of a porous ceramic material, a porous metal material, a porous polymer material or a porous wood material, most preferredly a porous wood material. One of the surfaces can be formed in this context by the same pressing tool that was used in preliminary draining. The opposing surface is preferably formed by one side of a plate of hardwood, preferably beech wood.

Compaction is suitably executed under a pressure of at least 20 MPa, preferably at least 30 MPa, even more preferredly at least 50 MPa, and up to 150 MPa.

When the preliminary draining and compaction is executed in one and the same step, the suspended powder mixture is transferred directly to the limited space, which is placed on the hard, porous surface in the mechanical pressing tool and drained and compacted by mechanical pressing at the pressure just stated. The final degree of compactness and final form of the ceramic product can be attained directly in this connection, in one and the same step. The final form of the product can here consist e.g. of a thin plate, on which electrical circuits can be arranged in a subsequent step, to produce circuit boards, biosensors or the like. With this embodiment it is preferable that the powder material and/or liquid contains a liquid-reducing agent, which means that a beech wood plate is sufficient for draining. However, it should not be excluded that a ceramic plate, or a plate of another hard, porous material, can be used in the mechanical pressing tool. A prerequisite here is naturally that the plate is capable of managing the pressure levels used.

The compacting tool in the press can consist of a preformed body/surface, the pressing giving the desired surface topography directly, which can be used advantageously for later replicas. The method is also applicable in the construction of complex structures, when single pressed plates with the surface topography obtained can be placed on one another. The plates are joined here in an early step in the hardening process. A light pressure on the structure means that the complex system is joined chemically in connection with continued and final hardening, which can be controlled timewise by the choice of accelerator and quantity of accelerator.

Possible Application in a Cavity

Compaction in the pressing tool can alternatively be completed with the precompacted cake of moist powder material being broken into pieces to be then packed together further in a final compaction step. This is the case e.g. if the ceramic material is to form a dental filling material or is to be packed together in a cavity of a different type. In a final compaction step of this kind, a quantity of the moist powder mixture is applied to a cavity, final compaction and the removal of any surplus liquid being carried out in situ by means of a compaction tool. The part of the compaction tool acting against the moist powder mixture suitably consists of a hard, porous material, into which any surplus liquid is sucked, at the same time as the moist powder mixture is compacted further in the cavity. The hard, porous material can consist of a porous ceramic material, a porous metal material, a porous polymer material or a porous wood material, most preferredly a porous wood material, e.g. hardwood material. However, the final compaction step can possibly be executed by way of introduction using a stopper of the traditional type, e.g. of steel, and by way of conclusion with a porous compaction device. The final compaction step can be executed by hand, suitably under a pressure of at least 30 MPa, preferably at least 40 MPa. The strength can be functionally developed as early as 10–60 minutes after final compaction.

When using the ceramic material as inorganic putty, draining/compacting in the pressing tool is preferably not used. Instead, final compaction and draining suitably take place directly in a cavity, e.g. a dent in a car panel which is to be evened out, the mass obtained following predraining being applied to the dent. In this connection, the pressing device suitably consists of a porous tool (spatula type, shaped "ruler" etc). The final degree of compaction can perhaps be permitted to be lower than for other applications in which pressing tools are used, e.g. 40–50 percent by volume solid phase. Major environmental advantages are foreseen in comparison with known types of putty. The material can also be used as building putty.

SUMMARY OF THE PROCESS FOR DIFFERENT APPLICATION

To sum up, for dental purposes initial predraining is used in two steps, i.e. self-draining on a porous plate and under light pressure. The preliminarily dewatered slurry is compacted and then drained further in a mechanical pressing tool with absorbent plate/plates, whereupon the cake obtained is broken into pieces and finally compacted in a tooth cavity. The very last compaction can be carried out here using a compacting device with an absorbent pressing surface.

For purposes in which the material is to be used as a putty, initial predraining is preferably used only in the form of self-draining on a porous plate. Liquid-reducing agents are suitably also used in this connection. Following predraining, the slurry assumes the form of a mass, which can be finally compacted and drained in a cavity, e.g. a dent in a car panel, preferably by means of a pressing device which suitably consists of a porous, absorbent tool (spatula type, shaped "ruler" etc.).

For purposes in which the material is not to be placed in a cavity, initial predraining is preferably used only in the form of self-draining on a porous plate, or in the same step as final compaction and draining. Liquid-reducing agents are suitably used. The final compaction and draining take place in a mechanical pressing tool on a porous plate.

Post-Treatment

Following compaction, the product is kept in a humid environment, preferably at a relative humidity >90% or in water at a raised temperature, up to 90° C., preferably between 30 and 70° C. When compaction is complete, subsequent polishing, e.g. smoothing, of a free surface of the chemically bound ceramic material formed can be carried out within 1 hour, for dental applications preferably within 10 minutes, even more preferredly within 3–7 minutes of final compaction. For dental material, the grinding is performed using a conventional dental grinding arrangement. For carrier material for electronic circuits, the grinding is carried out in a manner suitable for this purpose, so that a good flatness and surface fineness is achieved. Following polishing, the material is allowed to finish hardening, preferably in a humid atmosphere or in water at a raised temperature.

BRIEF DESCRIPTION OF DRAWINGS

Some of the aspects according to the invention will be described further below with reference to the enclosed drawings, which are given by way of illustration only, and thus are not limitative of the present invention, and of which.

DETAILED DESCRIPTION OF DRAWINGS

Figure 1A:
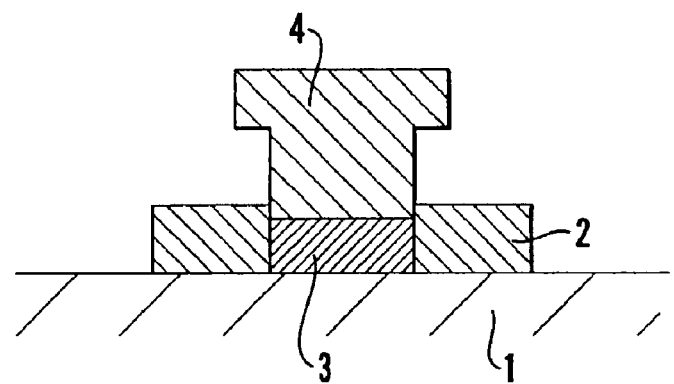
FIGS. 1a–c shows the steps and in this connection the arrangement used, seen in cross-section from the side, for the manufacture of the ceramic material.

FIG. 1a shows a hard, porous plate 1 of ceramic material, on which a ring 2 of e.g. plastic or plexiglass, with circular cylindrical walls, has been placed. The suspended powder material is poured down into the delimited space 3 defined by the walls of the ring 2 and the upper surface of the plate 1. The porous material in the plate 1 begins immediately to absorb a surplus of liquid from the slurry. A pressing device 4 of beech wood, which is formed with a first part which is dimensioned according to the space 3, so that it can be guided down into the same, can be used for certain applications. The inner diameter of the ring 2 can be typically 5–10 mm if the ceramic material is to be used for dental purposes, and 2–7 cm if the ceramic material is to be used as a carrier material for electrical circuits. The pressing tool 4 can possibly, but not necessarily, be provided with a larger surface on its second part, e.g. in the form of a cap. A light pressure, preferably 10 MPa maximum, is applied to the upper surface of the pressing device (the cap), e.g. by pressing with a thumb or hand, the effect of preliminary draining being increased.

Figure 1B:
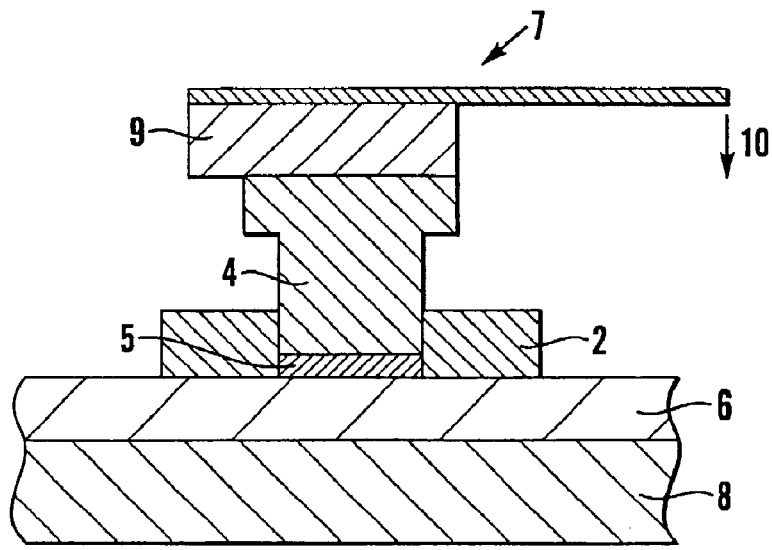

Following preliminary draining, the slurry has assumed the form of a cake. The ring 2, the moist powder cake 5 and the pressing device 4 are then lifted from the plate 1 and moved to another hard, porous plate 6 which is disposed in a pressing tool 7, see FIG. 1b. This second plate 6 preferably consists of a beech wood plate. The pressing tool 7 is shown only symbolically and comprises a bottom part 8, which provides support for the plate 6, an upper part 9, which is pressed against the pressing device 4, and possibly a handle 10, at least if the pressing tool is intended to be operated manually. If the pressing tool is intended to be operated automatically, pressing suitably takes place hydraulically instead. Compaction of the powder cake 5 takes place in the pressing tool 7 with simultaneous draining of a surplus of liquid, which is absorbed into the plate 6 and into the pressing device 4. The pressure used is at least 20 MPa, preferably at least 30 MPa, even more preferredly at least 50 MPa, and up to 150 MPa, depending on whether compaction takes place manually or mechanically.

Figure 1C:
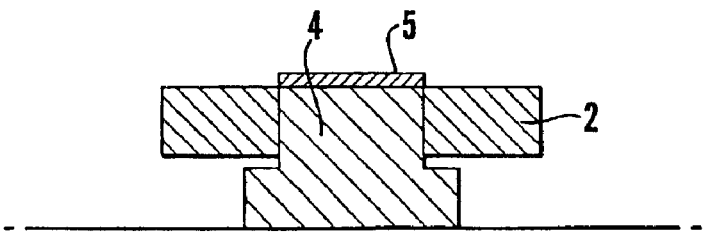

When compaction in the pressing tool 7 has been completed, the ring 2, powder cake 5 and pressing device 4 are lifted off the plate 6. The whole arrangement is then turned upside-down, so that the powder cake 5 can be released from the ring 2 by pressing the ring against the base or against the cap of the pressing tool 4, FIG. 1c. In automatic draining and compaction, it is suitable to use the same functional parts as in FIG. 1a. However, detachment of the cake (plate) is carried out using a traditional ejector.

The powder cake 5 is now ready to be broken into pieces and packed together in a cavity according to the previous description, or also it is fully finished and ready-compacted. The powder cake, or the powder cake packed into a cavity, is ground or polished according to the previous description, following which it only needs to lie and harden, suitably in a humid environment.

EXAMPLES

A series of experiments was performed to study the effect on expansion, in particular long-term expansion, of various expansion-compensating additives.

Description of Raw Materials:

Calcium aluminate of the phases $CaO.Al_2O_3$ and $CaO.2Al_2O_3$ forming part of e.g. Ca-aluminate cement (Alcoa or LaFarge), standard cement (Cementa), fine-grained silicon dioxide (Aldrich) and glass spheres (Sil-cell, Stauss GmbH). $Al_2O_3$ (Sumitomo, AKP 30), $ZrO_2$ (3-mol % $Y_2O_3$) from Toyo Soda.

Porous particles, produced in-house from fine-grained Al oxide (Sumitomo, AKP 30) (aggregate diameter approx. 15 micrometers)

The Examples under a)–h) Describe
a) calcium aluminate's long-term expansion with completely hydrated aluminate without additives, but with hardness-providing filler particles (reference)
b) effect of fine granularity of raw cement materials
c) effect of secondary phase, OPC cement
d) effect of secondary phase, fine-grained Si oxide
e) effect of porous aggregate on b)
f) effect of porous aggregate on c)
g) effect of a combination of OPC and fine-grained Si oxide
h) effect of a combination of various additives
i) effect of Si-containing secondary phases on a pure cement system without hardness-providing filler particles
j) effect of hardness-providing filler particles on i)

Calcium aluminates, $CaO.Al_2O_3$ and $CaO.2Al_2O_3$, with a molecular ratio of approx. 1:1 are mixed with filler particles and secondary additives (all quantities specified are in relation to the quantity of calcium aluminate) as stated below. When "aluminium oxide" is referred to, without the type of particles being specified, conventional hardness-providing filler particles are meant a) Addition of 40 percent by volume aluminium oxide, grinding time 24 h. The cement was ground for 20 h beforehand.
b) Addition of 40 percent by volume aluminium oxide, grinding time 24 h. The cement was ground for 80 h beforehand.
c) Addition of 40 percent by volume aluminium oxide, grinding time 24 h. The cement was ground according to b) above beforehand. 15 percent by volume OPC (ordinary Portland cement/standard cement) was added to the calcium aluminate.
d) Addition of 40 percent by volume aluminium oxide, grinding time 24 h. A secondary phase in the form of 10 percent by volume fine-grained silicon dioxide was added to calcium aluminate ground according to b) above.
e) Addition of 20 percent by volume aluminium oxide, grinding time 24 h. The cement was ground according to b) above. 20 percent by volume of porous aluminium oxide aggregates(produced in-house) was added only after a grinding time of 20 h.
f) Addition of 20 percent by volume aluminium oxide+20 percent by volume aluminium oxide as porous particles (aggregates), grinding time 24 h, but the aggregates were only added after 20 h. The cement was ground according to b) above, but with the addition of a secondary phase in the form of 15 percent by volume OPC.
g) Addition of 40 percent by volume aluminium oxide, grinding time 24 h. The cement was ground according to b) above. 5 percent by volume of OPC and 5 percent by volume of fine-grained silicon dioxide were added to the calcium aluminate.
h) Addition of 20 percent by volume aluminium oxide+20 percent by volume aluminium oxide as porous particles, grinding time 24 h, but the aggregates were only added after 20 h, however. A secondary phase in the form of 5 percent by volume of OPC and 5 percent by volume of fine-grained silicon dioxide and 0.5 percent by volume of glass spheres was added to the calcium aluminate in this case.
i) Addition of secondary phases in the form of 5 percent by volume of OPC and 5 percent by volume of fine-grained silicon dioxide, grinding time 24 h. The cement was ground beforehand for 80 h.
j) Addition of secondary phases in the form of 5 percent by volume of OPC and 5 percent by volume of fine-grained silicon dioxide and hardness-providing filler particles of $ZrO_2$ of 10 percent by volume, grinding time 24 h. The cement was ground beforehand for 80 h.

The mixtures were ground in a ball mill with inert grinding balls of silicon nitride with a coefficient of fullness of 35%. Isopropanol was used as a liquid. Following evaporation of the solvent, materials a)–h) were admixed with water, dewatered and tamped with a stopper into holes with a diameter of 4 mm in a container that permitted measurement of the dimensions in an optical microscope. The materials were kept moist at 37° C. between test measurements, which were performed continuously up to 180 days.

The results are reported in the table below.

| Sample description | Expansion in % after | | | | |
|---|---|---|---|---|---|
| | 1 d | 20 d | 80 d | 120 d | 180 d |
| a | 0 | 0.12 | 0.68 | 0.82 | 0.83 |
| b | 0 | 0.22 | 0.41 | 0.48 | 0.48 |
| c | 0 | 0.11 | 0.23 | 0.26 | 0.26 |
| d | 0 | 0.12 | 0.13 | 0.13 | 0.13 |
| e | 0 | 0.15 | 0.18 | 0.21 | 0.21 |
| f–j | all values under 0.10% | | | | |

Error margin for measurements +−0.02%

Error margin measurement +0.02%

It is evident from the results that expansion stagnates after approx. 100 days. For the very dimensionally stable materials (expansion under 0.15% including error margins) no clear point in time for stagnation can be deduced. It is also evident that Only an increased grinding time (b) in relation to reference (a) almost halves long-term expansion.

When a secondary phase in the form of OPC cement in a quantity of 15 percent by volume is also added (c), a further virtual halving of long-term expansion is achieved in relation to (b).

Long-term expansion is further reduced by a secondary phase in the form of fine-grained silicon dioxide in a quantity of 10 percent by volume (d).

Improved (reduced) long-term expansion in relation to (b) is also achieved using porous aggregates of aluminium oxide in a quantity of 20 percent by volume (e).

Extremely low expansion was achieved when using porous particles and a secondary phase of OPC cement in combination.

Extremely low expansion was achieved when using a secondary phase of both OPC cement and fine-grained silicon dioxide, in combination.

Extremely low expansion was achieved when using porous particles, a secondary phase of both OPC cement and fine-grained silicon dioxide and glass spheres in combination.

Extremely low expansion was achieved for the pure cement system without hardness-providing filler particles when using only a low content of Si-containing additives.

Extremely low expansion was achieved for the Ca-aluminate system with low quantities (10 percent by volume) of hardness-providing filler particles, using only Si-containing additives for expansion compensation.

The materials which have extremely low expansion (<0.10%) have, apart from the expansion properties, a general feature profile which matches the corresponding cement system without additives. These materials have a compressive strength of 170–200 MPa, hardness of H (Vickers 100 g)=110–130 and an extremely high acid resistance.

The invention is not restricted to the embodiments described, but can be varied within the scope of the claims. When using the invention as a carrier material for electronic circuits, as a carrier material in micromechanical applications, as a carrier material for biosensors or as a carrier material for optical fibres for producing circuit boards, biosensors or the like, it is also conceivable that the product does not need to include expansion-compensating additives, which however falls outside the scope of the present invention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing a chemically bound ceramic material by reacting a binding phase of one or more powdered binding agents and a hydration liquid reacting with these binding agents, a quantity of powder containing said binding phase being suspended in said hydration liquid so that all powder grains are brought into close contact with the hydration liquid, draining the slurry thus obtained so that the majority of the surplus reacting hydration liquid is removed, compacting the slurry during final draining, before hardening the material by reaction between said binding phase and the remaining hydration liquid, wherein one or more expansion-compensating additives, are mixed into said powdered binding phase, prior to or in connection with its suspension in the liquid and wherein said binding phase comprises calcium aluminate cement, wherein a compression strength of said chemically bound ceramic material is in the range of 170–200 MPa.

2. The method according to claim 1, wherein the material is substantially free from hardness-providing filler particles.

3. The method according to claim 1, wherein the material is made to contain up to 50 percent by volume ballast material, which is mixed in said binding phase, prior to or in connection with suspension of said binding phase in the liquid.

4. The method according to claim 1, wherein said additives consist of one or more additives selected from the group consisting of porous particles or porous aggregates, soft particles which have an E-modulus which is lower than the E-modulus of the binding phase, and a secondary phase, which secondary phase reacts with the binding phase.

5. The method according to claim 4, wherein said additives comprise a secondary phase, said secondary phase consisting of Portland cement and/or fine crystalline silicon dioxide and/or another Si-containing phase.

6. The method according to claim 5, wherein said secondary phase consists of Portland cement in a quantity of 1–5 percent by volume and/or fine crystalline silicon dioxide in a quantity of 1–5 percent by volume.

7. The method according to claim 6, wherein said additives comprise porous particles or porous aggregates, that comprise oxides of Al, Zr, Ti, Si, Sn or Zn.

8. The method according to claim 4, wherein said additives at least substantially consist of porous particles, which porous particles comprise microspheres with a closed porosity, having a porosity which exceeds 50%, and which microspheres are present in quantities of less than 2 percent by volume of the raw compact.

9. The method according to claim 1, wherein said binding agents have a grain size of 2–8 $\mu$m, which is achieved by grinding.

10. The method according to claim 1, wherein the powder mixture and/or the liquid comprises an accelerator for accelerating the reaction between said binding agent and the liquid.

11. The method according to claim 1, wherein the powder mixture or hydrating liquid comprises a liquid-reducing agent in an amount of at least 0.1%.

12. The method according to claim 1, wherein the preliminary draining is executed using a hard, porous material, the slurry being placed in a delimited space on said porous material, so that a surplus of the liquid is absorbed into the porous material.

13. The method according to claim 1, wherein the preliminary draining is executed under pressure.

14. The method according to claim 12, wherein the preliminary draining is performed by self-draining, under the inherent pressure of the slurry.

15. The method according to claim 1, wherein said compaction is executed mechanically using a pressing tool which comprises at least one surface acting against the moist powder mixture.

16. The method according to claim 15, wherein said compaction is executed under a pressure of at least 20 MPa.

17. The method according to claim 1, wherein said compaction, as a final compaction step, comprises applying a quantity of the moist powder mixture to a cavity, performing final compaction and the removal of any surplus liquid in situ by means of a compaction device, the component of which acting against the moist powder mixture comprises a porous material, into which any surplus liquid is absorbed, at the same time as the moist powder mixture is compacted further in the cavity.

18. The method according to claim 17, wherein said final compaction step is executed under a pressure of at least 30 MPa.

19. The method according to claim 1, wherein said draining and compaction is performed in one and the same step, under a pressure of at least 20 MPa, under a dolly of a hard, porous material, into which a surplus of liquid is absorbed during draining and compaction, which hard, porous material comprises a porous ceramic material, a porous metal material, a porous polymer material or a porous wood material.

20. The method according to claim 1, wherein the compaction is executed to a degree of compactness of 40–60 percent by volume of the solid phase.

21. The method according to claim 1, further comprising subsequent polishing of a free surface of the chemically bound ceramic material formed.

22. A chemically bound ceramic material produced according to claim 1.

23. The method according to claim 5 wherein said secondary phase is present in a total quantity of 1–20 percent by volume in the raw compact.

24. The method according to claim 7, wherein said porous particles or porous aggregates have a diameter of 2–30 $\mu$m and an open porosity of 20–60%, the pore openings in the particles/aggregates being less than 5 μm.

25. The method according to claim 7, wherein said porous particles or porous aggregates have a diameter of 5–15 μm, an open porosity of 20–60%, and the pore openings in the particles/aggregates are less than 5 μm.

26. The method according to claim 7, wherein said porous particles or porous aggregates have a diameter of 5–15 μm, and an open porosity 30–50%, the pore openings in the particles/aggregates being less than 5 μm.

27. The method according to claim 7, wherein said porous particles or porous aggregates have a diameter of 5–15 μm, an open porosity of 20–60%, and the pore openings in the particles/aggregates are in the range of 0.1–5 μm.

28. The method according to claim 7, wherein said porous particles or porous aggregates have a diameter of 5–15 μm, an open porosity of 20–60%, and the pore openings in the particles/aggregates are in the range of 1–3 μm.

29. The method according to claim 8, wherein said additives comprise porous particles, which porous particles comprise glass microspheres with a closed porosity that exceeds 80%, and are present in quantities of less than 2 percent by volume of the raw compact.

30. The method according to claim 8, wherein said additives comprise porous particles, which porous particles comprise glass microspheres with a closed porosity that exceeds 50%, and are present in quantities of 0.1–2 percent by volume of the raw compact.

31. The method according to claim 8, wherein said additives comprise porous particles, which porous particles comprise glass microspheres with a closed porosity that exceeds 50%, and are present in quantities of 0.5–1.5 percent by volume of the raw compact.

32. The method according to claim 9, wherein said binding agents have a grain size of 3–4 μm, which is achieved by grinding.

33. The method according to claim 10, wherein the powder mixture and/or the liquid is made to contain an accelerator for accelerating the reaction between said binding agent and the liquid.

34. The method of claim 33, wherein the accelerator is a salt of an alkali metal, and is present in the liquid in an amount of 0.2–2 g/L.

35. The method of claim 32, wherein the accelerator is present in the solid in an amount of 0.1–0.5 per ml per volume of the powder mixture, calculated on the solid content.

36. The method according to claim 11, wherein the powder mixture or hydrating liquid is made to contain a liquid-reducing agent that is a lignosulfonate, citrate, hydroxycarboxyl-containing agent and/or EDTA.

37. The method of claim 32, in which the liquid-reducing agent is present in the hydrating liquid in a quantity exceeding 0.1%.

38. The method according to claim 37, wherein the liquid-reducing agent is present in an amount of 0.1–0.5%.

39. A chemically bound ceramic material that is used as a dental material comprising the chemically bound ceramic material according to claim 22.

40. The material of claim 39 that is a dental filling material.

41. A chemically bound ceramic material that is used as a carrier material for electronic circuits or micromechanical applications or for a biosensor comprising the chemically bound ceramic material according to claim 22.

42. A chemically bound ceramic material that is used as a carrier material for optical fibers comprising the chemically bound ceramic material according to claim 22.

43. A chemically bound ceramic material that is used as a material for casting or replication comprising the chemically bound ceramic material according to claim 22.

44. A chemically bound ceramic material that is used as a filler putty comprising the chemically bound ceramic material according to claim 22.

45. The method according to claim 12, in which the porous surface is formed by a porous ceramic material, a porous metal material, a porous polymer material or a porous wood material.

46. The method of claim 13, wherein the pressure for the preliminary draining is a maximum of 10 MPa.

47. The method of claim 15, in which the pressing tool comprises at least two surfaces acting against the moist powder mixture.

48. The method of claim 15, in which the surface formed of a hard, porous material is formed by a porous ceramic material, a porous metal material, a porous polymer material or a porous wood material.

49. The method according to claim 15, wherein said compaction is performed under a pressure of from 50 to 150 MPa.

50. The method of claim 18, wherein the final compaction step is performed under a pressure of at least 40 MPa.

51. The method of claim 19, in which the draining and compaction are performed under a pressure of from 30 MPa to 150 MPa.

52. The method of claim 20, wherein the compaction is performed to a degree of compactness of greater than 51 to 60 percent by volume of the solid phase.

53. The method of claim 20, wherein the compaction is performed to a degree of compactness of 40 to 50 percent of by volume of the solid phase.

54. The method of claim 21 wherein a free surface of the chemically bound ceramic material is polished within one hour of the compaction being completed.

* * * * *